(12) United States Patent
Yan

(10) Patent No.: US 7,841,346 B2
(45) Date of Patent: Nov. 30, 2010

(54) METHOD AND DEVICE FOR MANDIBULAR ADVANCEMENT

(75) Inventor: Guoping Yan, Murrumbeena (AU)

(73) Assignee: Quiesco Pty. Ltd., Victoria (AU)

( * ) Notice: Subject to any disclaimer, the term of this patent is extended or adjusted under 35 U.S.C. 154(b) by 0 days.

(21) Appl. No.: 11/813,624

(22) PCT Filed: Jan. 9, 2006

(86) PCT No.: PCT/AU2006/000023

§ 371 (c)(1),
(2), (4) Date: Jul. 10, 2007

(87) PCT Pub. No.: WO2006/072147

PCT Pub. Date: Jul. 13, 2006

(65) Prior Publication Data

US 2008/0035157 A1 Feb. 14, 2008

(30) Foreign Application Priority Data

Jan. 10, 2005 (AU) .............................. 2005900090

(51) Int. Cl.
*A61C 5/14* (2006.01)
*A61C 3/00* (2006.01)
(52) U.S. Cl. .......................................... 128/861; 433/7
(58) Field of Classification Search ................. 128/848, 128/857, 859, 861; 433/6, 7, 68–69, 140, 433/18, 19, 33, 49
See application file for complete search history.

(56) References Cited

U.S. PATENT DOCUMENTS

| 4,466,794 | A | * | 8/1984 | Roup | ............................ 433/69 |
| 5,117,816 | A | | 6/1992 | Shapiro et al. | |
| 5,810,013 | A | * | 9/1998 | Belfer | ......................... 128/848 |
| 5,823,194 | A | | 10/1998 | Lambert | |
| 5,829,441 | A | | 11/1998 | Kidd et al. | |
| 6,170,485 | B1 | | 1/2001 | Orrico | |
| 6,408,851 | B1 | * | 6/2002 | Karell | .......................... 128/848 |
| 6,450,167 | B1 | * | 9/2002 | David et al. | .................. 128/848 |
| 7,311,103 | B2 | * | 12/2007 | Jeppesen | ................ 128/201.26 |

(Continued)

FOREIGN PATENT DOCUMENTS

AU        770465  B2      2/2004

(Continued)

OTHER PUBLICATIONS

English translation of JP 200390358 Oct. 2003.*

*Primary Examiner*—Patricia M Bianco
*Assistant Examiner*—Tarla R Patel
(74) *Attorney, Agent, or Firm*—Hogan Lovells US LLP

(57) ABSTRACT

An orthotic device (100) for retaining a patient's mandible in an advanced or protrusive position comprises an intraoral anterior mandibular abutment surface (125) for resisting mandibular retraction by abutting the gingiva covering the mandible and an extramaxillary anterior maxillary abutment surface (115) against which the intraoral anterior mandibular abutment surface (125) is braced. In order to resist rotation of the dental orthotic produced by the interaction of the intraoral anterior mandibular abutment surface and the extramaxillary anterior maxillary abutment surface, the orthotic device is provided with an intraoral posterior maxillary abutment surface (140). The relative positions of the maxillary and/or mandibular abutment surfaces may be adjusted to suit the requirements of the user.

29 Claims, 14 Drawing Sheets

U.S. PATENT DOCUMENTS

2003/0234022 A1 12/2003 Belfer
2005/0028827 A1* 2/2005 Halstrom .................... 128/861

FOREIGN PATENT DOCUMENTS

| JP | 2003290358 A | * | 10/2003 |
| JP | 20030290358 A | | 10/2003 |
| WO | 9423673 A1 | | 10/1994 |
| WO | 0152928 A1 | | 7/2001 |
| WO | 0238090 A1 | | 5/2002 |

* cited by examiner

METHOD AND DEVICE FOR MANDIBULAR ADVANCEMENT

CROSS-REFERENCE TO RELATED APPLICATIONS

This application is the U.S. National Phase under 35 U.S.C. §371 of International Application PCT/AU2006/000023, filed on Jan. 9, 2006, which claims priority to Australian Patent Application No. 2005900090, filed on Jan. 10, 2005. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

The present application claims priority from Australian Provisional Patent Application No. 2005900090 filed on 10 Jan. 2005, the content of which is incorporated herein by reference.

FIELD OF THE INVENTION

The present invention relates to a dental orthotic and methods of using a dental orthotic. In particular the present invention relates to a method and device for retaining the mandible in protrusive position.

BACKGROUND TO THE INVENTION

During normal breathing, air passes through the nose and past the flexible structures in the back of the throat such as the soft palate, uvula and tongue. When an individual is awake, muscles hold the airway open, but during sleep, these muscles relax and can potentially cause problems. Sleep disordered breathing such as snoring, upper airway resistance syndrome (UARS) and obstructive sleep apnoea (OSA) are thought to occur when there is at least partial occlusion of the airway, with the tongue often being associated with the occlusion. During OSA, the tongue is sucked against the back of the throat, completely blocking the air flow. When oxygen levels in the brain become low enough, the sleeper partially awakens and the muscles contract opening the airway again. This cyclic occlusion of the airway can have serious repercussions, including contributing to cardiovascular diseases potentially leading to cardiac arrest and death.

There are a number of treatment options available including surgery, nasal continuous positive airway pressure (CPAP) and the use of orthotic devices. Orthotic devices are becoming an increasingly favoured option as they are generally small and easy to wear and relatively inexpensive. Another benefit of orthotic devices is that the treatment is reversible and non-invasive.

Mandibular advancement device (MAD) is one type of orthotic device which is used to hold the mandible in a protrusive position, which has proved effective in the treatment of sleep disordered breathing. Retaining the mandible in a protruded position has been found to help control the symptoms of sleep disordered breathing by clearing the airways and reducing the likelihood of the tongue impacting on breathing.

Boil and bite MADs are prefabricated and are lined with a soft, thermoplastic material that is moulded to the patient's teeth in the patient's home. The MAD engages the mandible mainly at the incisors and therefore applies the force of advancement across only a couple of teeth. While these MADs are relatively cheap and easy to use, they have the disadvantage in that they can potentially apply excessive force to the lower anterior teeth in some patients and this can cause discomfort, movement of the teeth and problems with the fit of the device over time. Another potential problem is that they are not adjustable once moulded to the patient, limiting their applicability to a wider range of patients. Furthermore, some patients may not have healthy gums and teeth in both the upper and lower jaws upon which to brace the MAD in the mouth.

Another example is a laboratory fabricated MAD which requires the attendance of a dentist to take mouth impressions which are used to make models of the teeth and gums. These moulds are then used to make dental overlays to overlay all of the lower and upper teeth, and protrude the mandible and help to clear the airways. A laboratory fabricated MAD can also cause excessive force on the teeth, leading to pain and tooth movement. Moreover, laboratory fabricated MADs can be problematic to customize to the patient's dental requirements as they require both healthy gums and teeth.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present invention provides a dental orthotic device for retaining a patient's mandible in a protrusive position, the dental orthotic device comprising:

an intraoral anterior mandibular abutment surface for resisting mandibular retraction by abutting the patient's gingiva covering the mandible;

an extramaxillary anterior maxillary abutment surface against which the intraoral anterior mandibular abutment surface is braced;

an intraoral posterior maxillary abutment surface to resist rotation of the dental orthotic produced by interaction of the intraoral anterior mandibular abutment surface and the extramaxillary anterior maxillary abutment surface.

In another aspect, the present invention provides a method of retaining a patient's mandible in a protrusive position, the method comprising:

resisting retraction of the mandible by abutting on the gingiva covering the mandible an intraoral anterior mandibular abutment surface;

bracing the intraoral anterior mandibular abutment surface against an extramaxillary anterior maxillary abutment surface; and bracing against rotation produced by the interaction of the intraoral anterior mandibular abutment surface and the extramaxillary anterior maxillary abutment surface, with an intraoral posterior maxillary abutment surface.

In yet a further aspect, the present invention provides a kit of parts comprising an intraoral anterior mandibular abutment surface, and/or an extramaxillary anterior abutment surface and/or an intraoral posterior maxillary abutment surface.

In one embodiment of the invention, the anterior maxillary abutment surface is concave and preferably the anterior maxillary abutment surface is of a shape to comfortably fit upon and conform to the shape of the tissue covering the maxillary bone. In another embodiment of the invention, the anterior maxillary abutment surface is extraoral and pushes on the soft tissue covering the subnasal maxillary bone.

In another embodiment of the invention, the anterior maxillary abutment surface is adjustably mounted on the orthotic device so that the extent of protrusion of the mandible can be controlled.

In yet another embodiment of the invention, the orthotic device comprises a tongue abutment surface which contacts the tongue when the mandible is in a protruded position. The tongue abutment surface may be adapted to retain the tongue in an anterior position, and/or a depressed position, to discourage the tongue from blocking the airway. In an alternative embodiment of the invention, the orthotic device may be shaped to give the tongue sufficient room for the comfort of the patient.

In a further embodiment of the invention, the intraoral anterior mandibular abutment surface is convex and in one embodiment, the abutment surface is formed of an elastomeric thermoplastic material which is of a shape to fit comfortably upon the gingiva covering the mandible. Preferably the intraoral anterior mandibular abutment surface is made from a silicone rubber.

In another embodiment of the invention, the orthotic device comprises at least one guide surface to resist lateral movement of the orthotic device in the patient's mouth. Preferably the orthotic device has at least two guide surfaces for positioning the orthotic device.

In yet a further embodiment, the orthotic device further comprises a soft palate abutment surface adapted to support the patient's soft palate, preferably the soft palate abutment surface is of a shape to conform to the surface of the soft palate.

In some preferred embodiments, the orthotic device is provided with air holes to facilitate airflow through the device.

In one embodiment, the orthotic device further comprises a tooth stabilizing plate adapted to be fitted to the lower dentition and/or upper dentition.

BRIEF DESCRIPTION OF THE DRAWINGS

Examples of the invention will now be described with reference to the accompanying drawings in which.

DETAILED DESCRIPTION OF THE PREFERRED EMBODIMENTS

As used herein, the "mandibular surface" is taken to include all things of, pertaining to or attached to the anterior portion of the lower jaw. Non-limiting examples of anterior mandibular surfaces include bone, gingiva or gum, teeth, prosthetics and other fixed or removable appliances.

As used herein, "maxillary surface" is taken to include all things of, pertaining to or attached to the upper jaw. Non-limiting examples of maxillary surfaces include bone, gum, teeth, prosthetics or other fixed or removable appliances.

Figure 1:
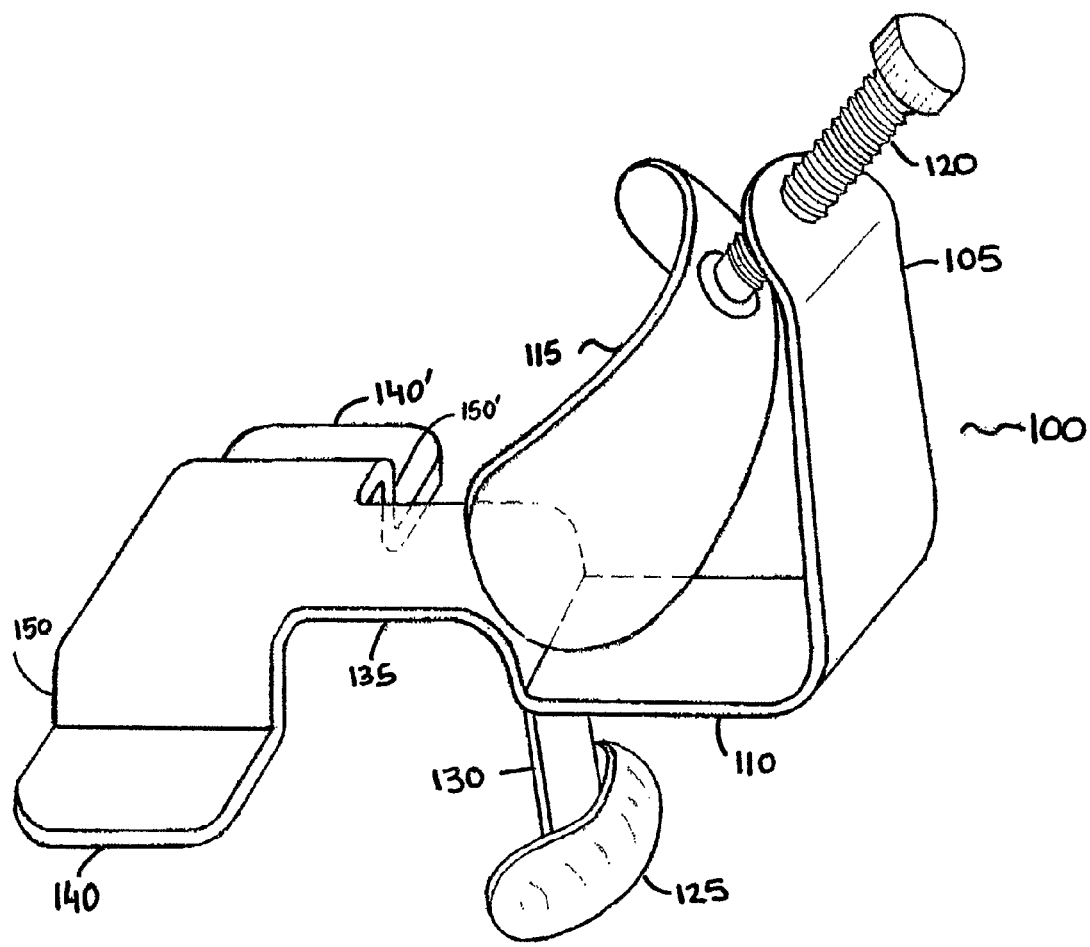
FIG. 1 is a perspective view of an orthotic device according to one embodiment of the invention.

Referring to the drawings, the orthotic device 100 of the embodiment illustrated in FIG. 1 incorporates an extraoral member 105 and an intraoral member 110 adapted to fit inside the mouth of the patient. The members 105 and 110 are made from stainless steel. Alternatively, such extraoral and intraoral members can be made from a rigid thermoplastic. Thermoplastic materials can be softened by heat to allow for manipulation of their shape, examples of suitable thermoplastic materials include acrylic, hard durometer, polypropylene, methyl vinyl acetate, ethyl vinyl acetate, polyethylene and hard durometer urethane.

A concave anterior maxillary abutment surface 115 is shown mounted to the member 105 by a threaded bolt 120. As illustrated, the anterior maxillary abutment surface 115 is slightly angled towards the lip to provide more uniform contact with the tissue covering the subnasal maxillary bone. The anterior maxillary abutment surface 115 is positioned such that it does not substantially impinge upon or obstruct flow of air through the nose.

In other embodiments of the invention, such an anterior maxillary abutment surface may be adjustably mounted to the orthotic device by a slide arrangement or any other means known in the art. In yet other embodiments, such an anterior maxillary abutment surface can be permanently affixed to the body of the orthotic.

In the embodiment of the invention shown in FIG. 1, the anterior maxillary abutment surface 115 is made from an elastomeric material that is of a shape to fit comfortably upon the soft tissue and skin covering the subnasal maxillary bone. Examples of suitable thermoplastic materials include caprolactone, polycaprolactone, 1,4-dibutanediol polyester, 2-oxepanone or silicone rubber.

The anterior mandibular abutment surface 125 of the embodiment of FIG. 1 is a convex band and is attached to member 110 by member 130. The anterior mandibular abutment surface 125 pushes on the gingiva covering the mandible. This arrangement allows the orthotic device 100 to be applied to patients who have lost one or more of their anterior mandibular teeth. Further, by abutting the gingiva covering the mandible, the anterior mandibular abutment surface 125 avoids or minimizes the chance of mandibular teeth being undesirably relocated over time.

In the embodiment of the invention illustrated in FIG. 1, the member 110 includes a deviation 135 to give the tongue sufficient room for the comfort of the patient. The intraoral posterior maxillary abutment surfaces 140 and 140' are flat projections which make contact with the maxillary surface.

The contact between the intraoral posterior maxillary abutment surfaces 140 and 140' and the maxillary surface helps resists rotation of the dental orthotic device 100 produced by the interaction of the anterior mandibular abutment surface 125 and the anterior maxillary abutment surface 115. The intraoral posterior maxillary abutment surfaces 140 and 140' are positioned such that they are unlikely to apply sufficient lateral force to the teeth to cause unwanted displacement of the teeth. The intraoral posterior maxillary abutment surfaces 140 and 140' are of a shape to comfortably conform to the patient's posterior maxillary characteristics. The two guide surfaces 150 and 150' are positioned to make loose contact with the maxillary surfaces, in other embodiments, the intraoral posterior maxillary abutment surfaces may make contact with the maxillary molars or premolars, to position the orthotic device in the mouth of the patient.

The degree of protrusion or advancement of the mandible can depend upon clinical requirements. The relative displacement of the mandible can be seen to have both side-to-side or forward-to-back components. Protrusion of the mandible carries the tongue forward so that (particularly in sleep) there is a reduced tendency for the tongue to impinge on the pharynx.

Figure 2:
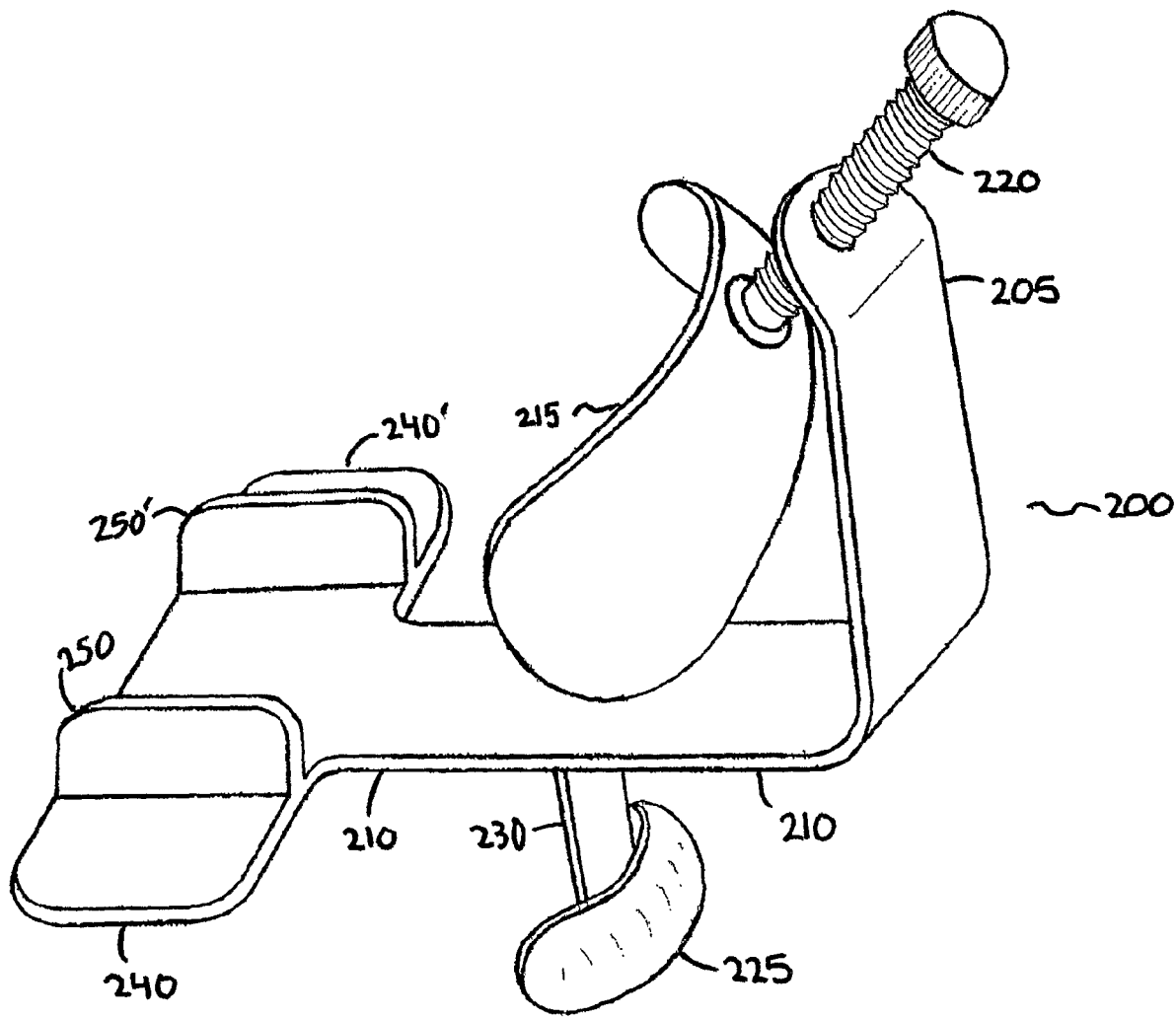
FIG. 2 is a perspective view of an orthotic device according to a second embodiment of the invention.

Referring to the second embodiment of the invention illustrated in FIG. 2, the orthotic device 200 incorporates a concave anterior maxillary abutment surface 215 mounted via a threaded bolt 220 to the extraoral member 205. The intraoral member 210 has a member 230 and an anterior mandibular abutment surface 225. The intraoral posterior maxillary abutment surfaces 240 and 240' are flat projections. The two guide surfaces may be positioned to make loose contact with the maxillary surfaces to resist lateral movement of the orthotic device 200. In yet further embodiments, such guide surfaces make loose contact with the maxillary molars or premolars. In other embodiments, the shape and configuration of such guide surfaces can be adjusted to fit the patient's requirements.

Figure 3:
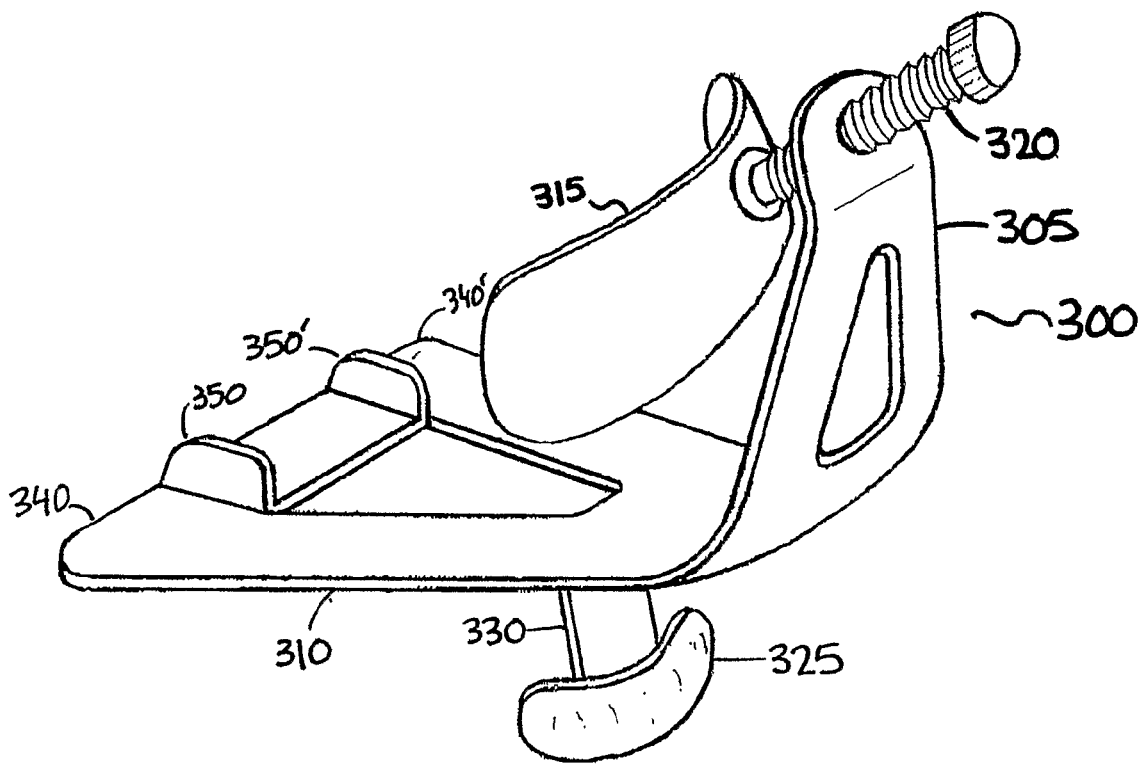
FIG. 3 is a perspective view of an orthotic device according to a third embodiment of the invention.

Referring to the third embodiment of the invention illustrated in FIG. 3, the orthotic device 300 incorporates a concave anterior maxillary abutment surface 315 mounted via a threaded bolt 320 to the extraoral member 305. The intraoral member 310 has a member 330, anterior mandibular abutment surface 325 and the two intraoral posterior maxillary abutment surfaces 340 and 340'. In this embodiment, the guide surfaces 350 and 350' are positioned to make loose contact with the maxillary surface. In other embodiments, such guide surfaces make contact with the maxillary molars or premolars to position and resist lateral movement of the orthotic device 300 in the mouth of the patient. Member 310 further forms a hole into which the patient's tongue may extend.

Figure 4:
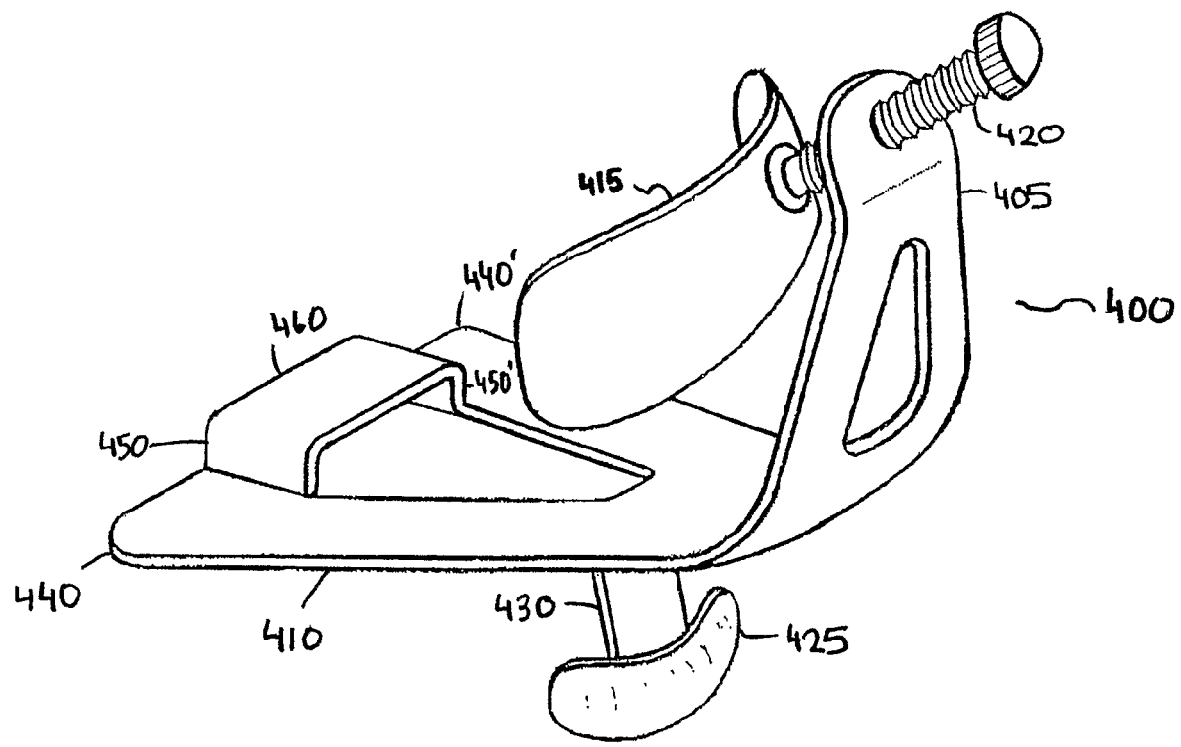
FIG. 4 is a perspective view of an orthotic device according to a fourth embodiment of the invention.

Referring to the fourth embodiment of the invention illustrated in FIG. 4, the orthotic device 400 incorporates a concave anterior maxillary abutment surface 415 mounted via a threaded bolt 420 to the extraoral member 405. The intraoral member 410 has a member 430, anterior mandibular abutment surface 425 and the two intraoral posterior maxillary abutment surfaces 440 and 440'. In this embodiment, the guide surfaces 450 and 450' are connected by a member 460 which is raised in order to give the tongue sufficient room for the comfort of the patient.

Figure 5:
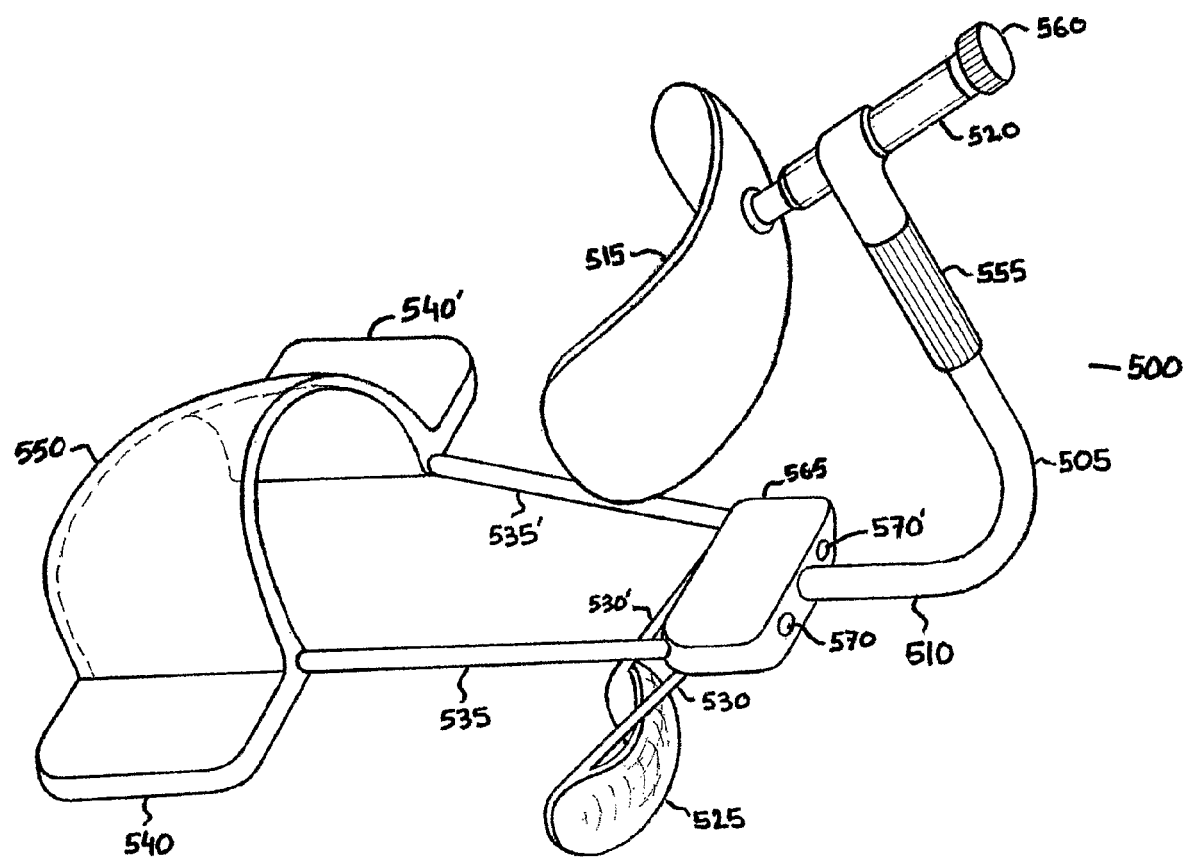
FIG. 5 is a perspective view of an orthotic device according to a fifth embodiment of the invention.

Referring to the fifth embodiment of the invention illustrated in FIG. 5, the orthotic device 500 incorporates a concave anterior maxillary abutment surface 515 mounted via a sliding arm 520 to the extraoral member 505. In this embodiment, the length of the arm is adjustable via the action of knob 560. In alternative embodiments, the knob may be substituted for another means for controlling the position of the concave anterior maxillary abutment surface. The other means may have facility for controlling the angle of an associated anterior maxillary abutment surface to suit the patient's needs and/or preference.

As illustrated, the length of the extraoral member 505 can be adjusted by the extraoral adjustment means 555. Alternatively, the length of such an extraoral member can be customized to the patient's needs when, for example, manufacturing the orthotic.

The extraoral member 505 is connected to the intraoral body portion 565 of the orthotic device by member 510. The length of member 510 can be adjusted to suit the patient's requirement(s). In this embodiment, air holes 570 and 570' are shown passing through intraoral portion 565 are positioned to improve the flow of air through and around the orthotic device 500. The incorporation of this feature has advantages for patients with breathing difficulties who, for example, may have nasal blockages or congestion.

The anterior mandibular abutment surface 525 is connected to portion 565 by members 530 and 530'. This variation gives the user's tongue more comfortable stretch space. In the illustrated embodiment, arms 530 and 530' are permanently affixed to the body portion 565. Alternatively, such arms may be adjustably mounted by a slide arrangement or other means known in the art.

As illustrated, the anterior mandibular abutment surface 525 is a convex band and pushes on the gingiva covering the mandible. In alternative embodiments, the anterior mandibular abutment surface is appropriately shaped to make contact with at least a portion of the anterior mandibular surface.

The intraoral posterior maxillary abutment surfaces 540 and 540' are connected to intraoral body portion 565 by arms 535 and 535'. This arrangement of arms 535 and 535' is advantageous in that it gives the user's tongue more room which may improve the comfort of the device. As illustrated, the abutment surfaces 540 and 540' are flat projections which make contact with at least a portion of the maxillary surface. This contact resists rotation of the orthotic device 500 produced by the interaction of the mandibular abutment surface 525 and the anterior maxillary abutment surface 515.

Surfaces 540 and 540' are separated by soft palate abutment surface 550. In the illustrated embodiment, the surface is arch shaped to conform to or support the patient's soft palate. This arrangement is useful for patients whose soft palate can potentially collapse during sleep. By also supporting the soft palate, in some situations the effectiveness of the orthotic device may be improved.

Figure 6:
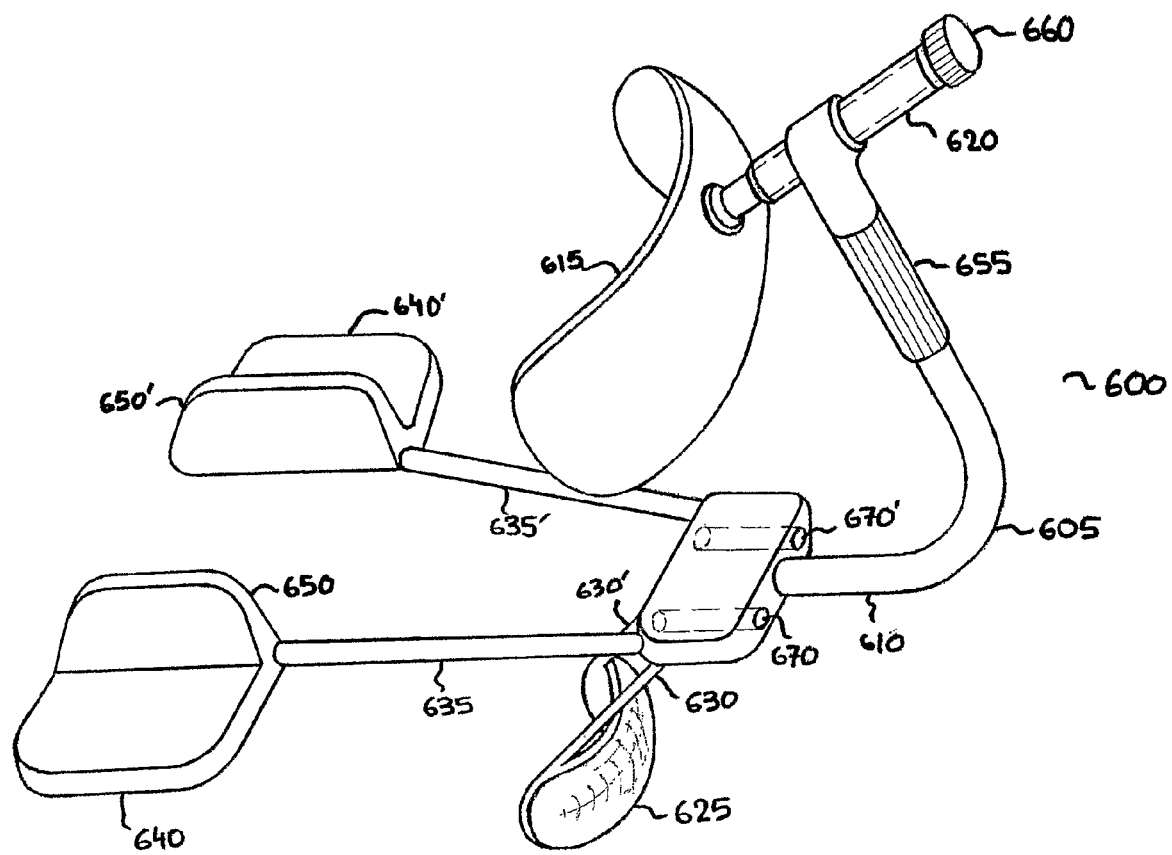
FIG. 6 is a perspective view of an orthotic device according to a sixth embodiment of the invention.

Referring to the sixth embodiment of the invention illustrated in FIG. 6, the orthotic device 600 incorporates a concave anterior maxillary abutment surface 615 mounted via a sliding arm 620 to the extraoral member 605. In this embodiment, the length of the arm is adjustable via the action of knob 660. As illustrated, the length of the extraoral member 605 can be adjusted by the extraoral adjustment means 655.

The extraoral member 605 is connected to the intraoral body portion 665 of the orthotic device by member 610. In this embodiment, air holes 670 and 670' passing through intraoral body portion 665 are positioned to improve the flow of air through and around the orthotic device. The convex band shaped anterior mandibular abutment surface 625 is connected to body portion 665 by members 630 and 630'.

The intraoral posterior maxillary abutment surfaces 640 and 640' are connected to intraoral body portion 665 by arms 635 and 635'. The abutment surfaces 640 and 640' are flat projections which make contact with at least a portion of the maxillary surface. This contact resists rotation of the orthotic device 600 produced by the interaction of the mandibular abutment surface 625 and the anterior maxillary abutment surface 615.

Abutment surfaces 640 and 640' have guide surfaces 650 and 650' respectively, which are positioned to make contact with the maxillary surfaces and help position the orthotic in the patient's mouth.

With this embodiment, there is no connecting member directly between the abutment surfaces 640 and 640'. This arrangement has the advantage that the user's tongue has more comfortable stretch space and is particularly useful for patients who do not have problems with the soft palate collapsing during sleep.

Figures 7A, 7B:
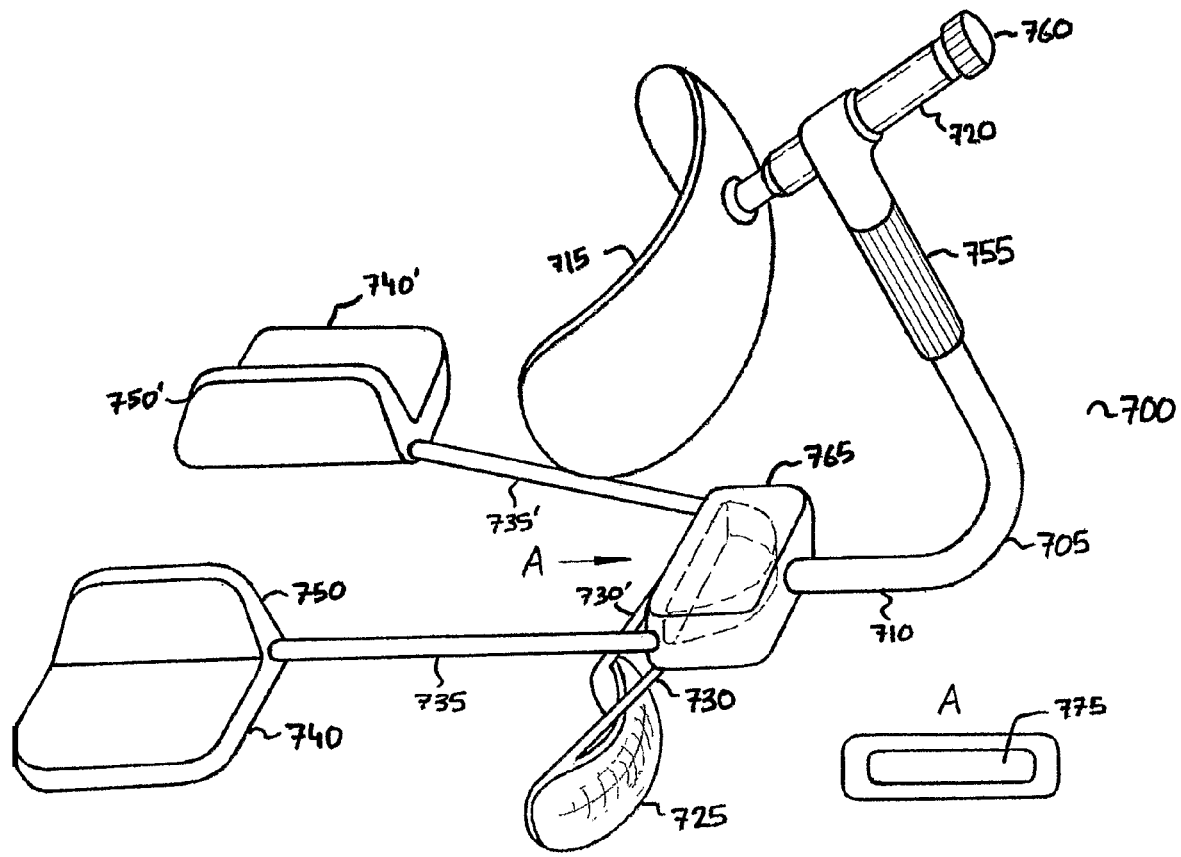
FIG. 7A is a perspective view of an orthotic device according to a seventh embodiment of the invention.
FIG. 7B is a front view along arrow A of the embodiment shown in FIG. 7A.

Referring to the seventh embodiment of the invention illustrated in FIG. 7A, the orthotic device 700 incorporates a concave anterior maxillary abutment surface 715 mounted via an adjustable arm 720 to the extraoral member 705. In this embodiment, the length of the arm 720 is adjustable via the action of knob 760. As illustrated, the length of the extraoral member 705 can be adjusted by the extraoral adjustment means 755.

The extraoral member 705 is connected to the intraoral body portion 765 of the orthotic device by member 710. The convex band shaped anterior mandibular abutment surface 725 is connected to body portion 765 by members 730 and 730'. The body portion 765 may be adapted to comfortably conform to the user's anterior maxillary and mandibular surfaces.

With the embodiment illustrated in FIG. 7A, the body portion 765 has a cavity 770. As shown in FIG. 7B, which is a view of the body portion 765 from direction A, the opening of the cavity 775 is which is adapted to allow the tongue an extended stretch space and is adapted to hold the tongue in a protrusive position. This arrangement advantageously improves the performance of the orthotic device in some patients.

The intraoral posterior maxillary abutment surfaces 740 and 740' are connected to intraoral body portion 765 by arms 735 and 735'. The abutment surfaces 740 and 740' are flat projections which make contact with at least a portion of the maxillary surface. This contact resists rotation of the orthotic device 700 produced by the interaction of the mandibular abutment surface 725 and the anterior maxillary abutment surface 715.

Abutment surfaces 740 and 740' have guide surfaces 750 and 750' respectively, which are positioned to make contact with the maxillary surfaces and help position the orthotic in the patient's mouth.

With this embodiment, there is no connecting member directly between the abutment surfaces 740 and 740'. This arrangement has the advantage that the user's tongue has more comfortable stretch space and is particularly useful for patients who do not have problems with the soft palate collapsing during sleep.

Figure 8:
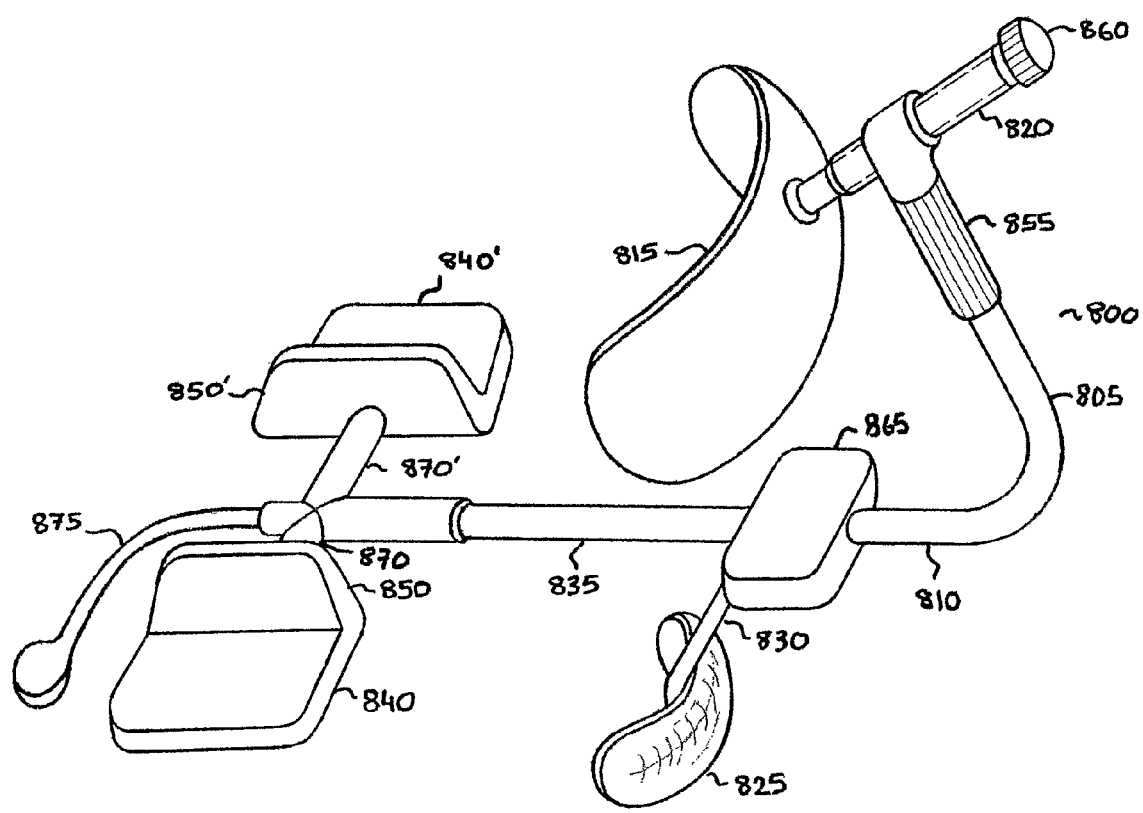
FIG. 8 is a perspective view of an orthotic device according to an eighth embodiment of the invention.

Referring to the eighth embodiment of the invention illustrated in FIG. 8, the orthotic device 800 incorporates a concave anterior maxillary abutment surface 815 mounted via a sliding arm 820 to the extraoral member 805. In this embodiment, the length of the arm 820 is adjustable via the action of knob 860. The length of the extraoral member 805 can be adjusted by the extraoral adjustment means 855.

The extraoral member 805 is connected to the intraoral body portion 865 of the orthotic device by member 810. The convex band shaped anterior mandibular abutment surface 825 is connected to body portion 865 by a single member 830.

The intraoral posterior maxillary abutment surfaces 840 and 840' are connected to intraoral body portion 865 by single arm 835 and by connecting arms 870 and 870'. The length of arm 835 may be adjusted to suit the patient's requirements. The abutment surfaces 840 and 840' are flat projections which make contact with at least a portion of the maxillary surface. This contact resists rotation of the orthotic device 800 produced by the interaction of the mandibular abutment surface 825 and the anterior maxillary abutment surface 815.

Abutment surfaces 840 and 840' have guide surfaces 850 and 850' respectively, which are positioned to make contact with the maxillary surfaces and help position the orthotic in the patient's mouth.

Attached to arm 835 is a posterior tail shaped portion 875 which is adapted to depress the user's tongue during sleep. This has the advantage in some patients of improving the performance of the orthotic device for treating sleep apnoea.

Figure 9:
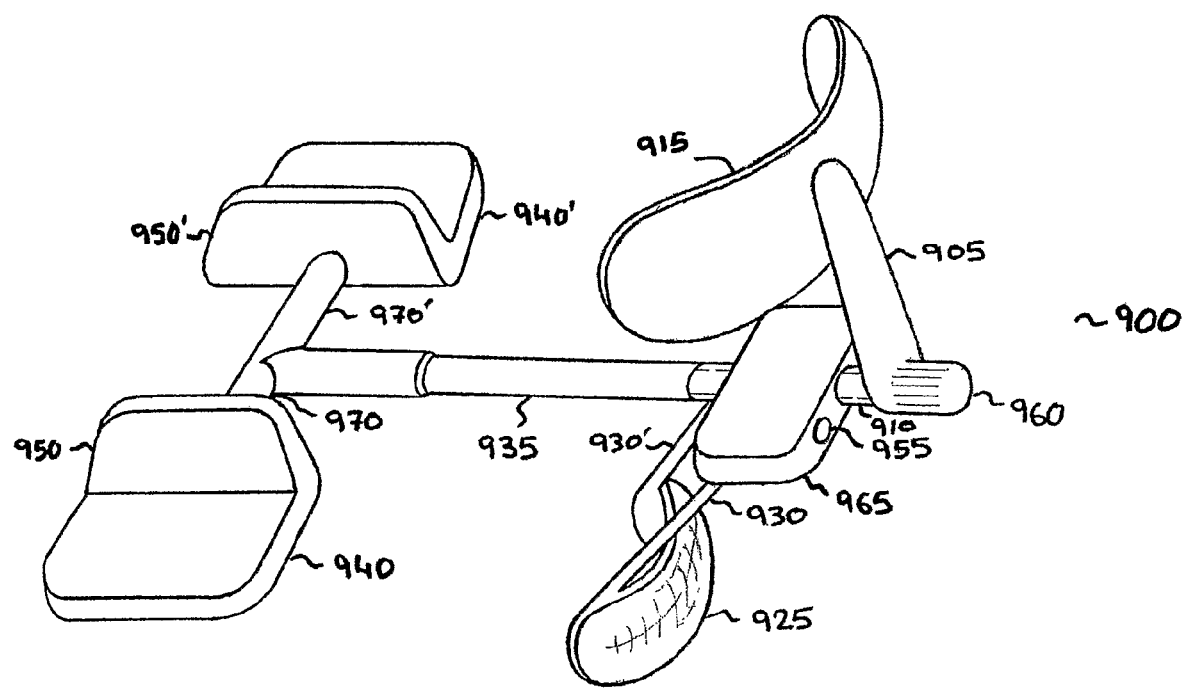
FIG. 9 is a perspective view of an orthotic device according to a ninth embodiment of the invention.

Referring to the ninth embodiment of the invention illustrated in FIG. 9, the orthotic device 900 incorporates an intraoral concave anterior maxillary abutment surface 915 mounted on intraoral member 905. While being intraoral, member 905 is nevertheless extramaxillary as required by the invention, by being adapted for positioning between the patient's top lip and maxillary. As illustrated, the position of the intraoral member 905 can be adjusted by the adjustment means 960.

The intraoral member 905 is connected to the intraoral body portion 965 of the orthotic device by member 910. The convex band shaped anterior mandibular abutment surface 925 is connected to body portion 965 by members 930 and 930'. The position of the convex band shaped anterior mandibular abutment surface 925 can be adjusted by movement of body portion 965 along member 910. The angle and/or length of members 930 and 930' can also be adjusted to suit the user's requirements. As illustrated, an air hole 955 is shown passing through intraoral body portion 965 and is positioned to improve flow of air through and around the orthotic device. The incorporation of this feature has advantages for patients with breathing difficulties who, for example, may have nasal blockages or congestion.

The intraoral posterior maxillary abutment surfaces 940 and 940' are connected to intraoral body portion 965 by single arm 935 and by connecting arms 970 and 970'. The length of arm 935 may be adjusted to suit the patient's requirements.

The abutment surfaces 940 and 940' are flat projections which make contact with at least a portion of the maxillary surface. This contact resists rotation of the orthotic device 900 produced by the interaction of the mandibular abutment surface 925 and the anterior maxillary abutment surface 915.

As illustrated, intraoral posterior maxillary abutment surfaces 940 and 940' have guide surfaces 950 and 950' respectively, which are positioned to make contact with the maxillary surfaces and help position the orthotic in the patient's mouth. In alternative embodiments, the guide surfaces are not need required.

Figures 10A, 10B:
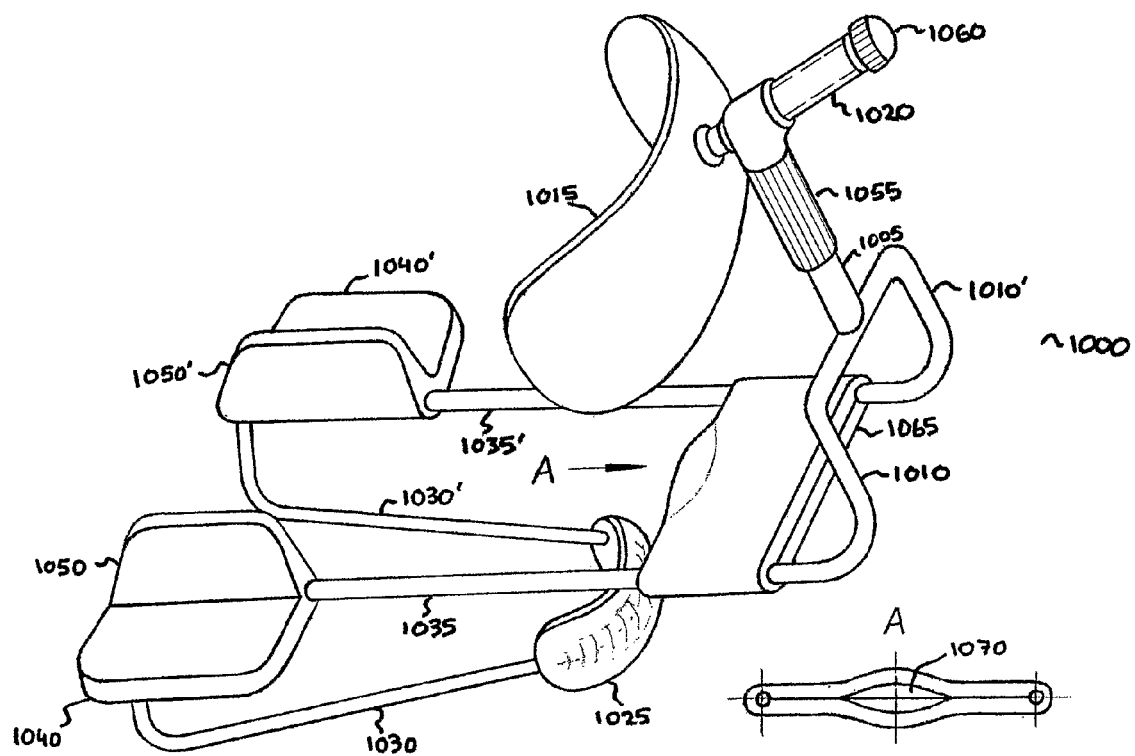
FIG. 10A is a perspective view of an orthotic device according to a tenth embodiment of the invention.
FIG. 10B is a front view along A of the embodiment shown in FIG. 10A.

Referring to the tenth embodiment of the invention illustrated in FIG. 10A, the orthotic device 1000 incorporates a concave anterior maxillary abutment surface 1015 mounted via an arm 1020 to the extraoral member 1005. In this embodiment, the length of the arm 1020 is adjustable via the action of knob 1060. Adjustability may also be provided by a turnbuckle mechanism (or jack screw mechanism) which can be operated by a turnbuckle key to advance or retract such an arm as desired. In this way, the appropriate treatment can be provided as determined by a clinician.

In other embodiments, the length of such an arm is fixed. As illustrated, the length of the extraoral member 1005 can be adjusted by the extraoral adjustment means 1055. Alternatively, the length of such an arm may be fixed.

The extraoral member 1005 is connected to intraoral arms 1035 and 1035' of the orthotic device by members 1010 and 1010'. In this embodiment, the intraoral body portion 1065 is made from an elastic band and is adapted such that the user's tongue can slip into cavity 1070, but not easily slip out of it. The cavity is shown in more detail in FIG. 10B along direction of arrow A. The combined biting forces from the anterior maxillary and mandibular surfaces and/or elastic tension can securely hold the tongue in a forward position. This can improve the effectiveness of the orthotic device in some patients.

The intraoral posterior maxillary abutment surfaces 1040 and 1040' are connected to intraoral arms 1035 and 1035'. The abutment surfaces 1040 and 1040' are flat projections which make contact with at least a portion of the maxillary surface.

The convex band shaped anterior mandibular abutment surface 1025 is connected to intraoral arms 1035 and 1035' by members 1030 and 1030'.

Abutment surfaces 1040 and 1040' have guide surfaces 1050 and 1050' respectively, which are positioned to make contact with the maxillary surfaces and help position the orthotic in the patient's mouth.

Figure 11:
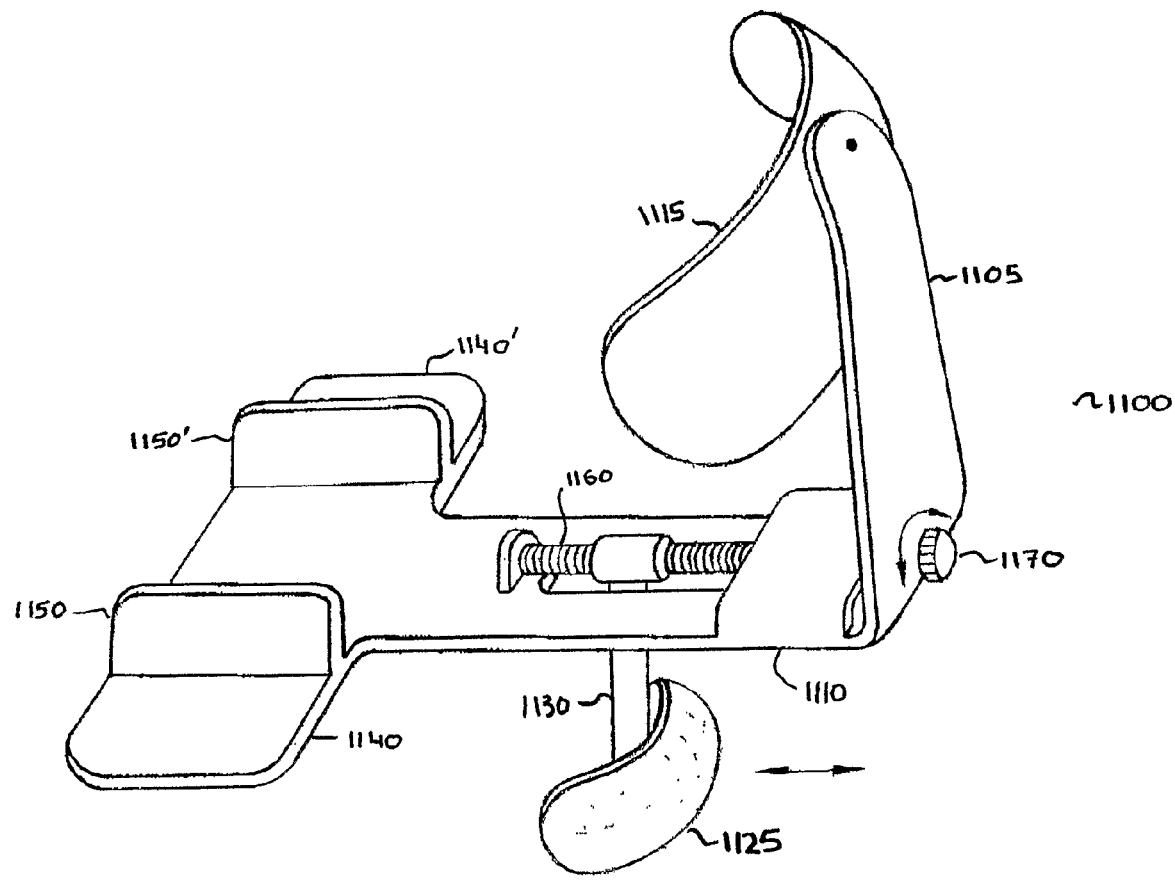
FIG. 11 is a perspective view of an orthotic device according to an eleventh embodiment of the invention.

Referring to the eleventh embodiment of the invention illustrated in FIG. 11, the orthotic device 1100 incorporates a concave anterior maxillary abutment surface 1115 mounted to the extraoral member 1105. The intraoral member 1110 has a positionally variable member 1130 and an attached anterior mandibular abutment surface 1125. The relative position of the surface 1125 can be varied by the action of knob 1170 and thread 1160. In alternative embodiments, the position of such a surface can be controlled by other means known in the art. By movement of the member 1125, the level of protrusion of the mandible can be controlled depending on the needs of the patient.

The intraoral posterior maxillary abutment surfaces 1140 and 1140' are flat projections with two guide surfaces 1150 and 1150' positioned to make loose contact with the maxillary surfaces to resist lateral movement of the orthotic device 1100.

Figure 12:
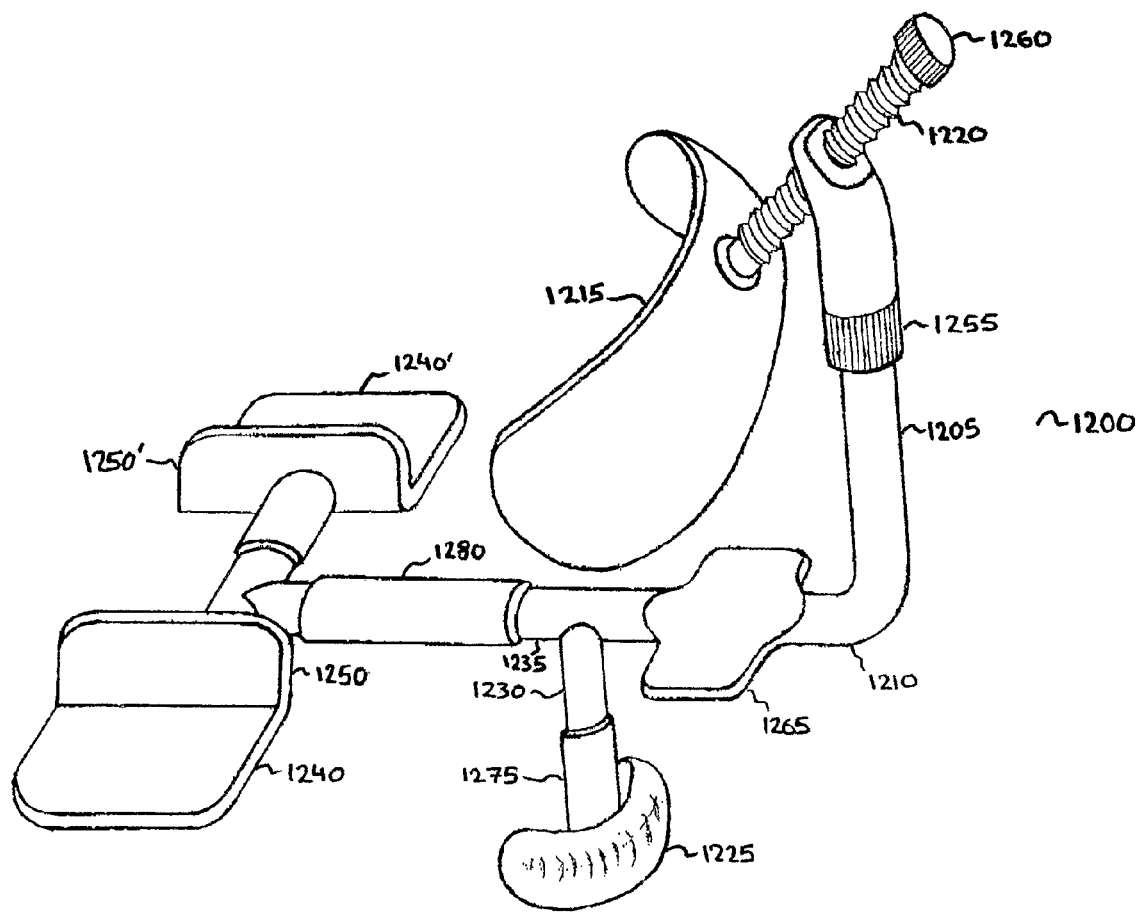
FIG. 12 is a perspective view of an orthotic device according to a twelfth embodiment of the invention.

Referring to the twelfth embodiment of the invention illustrated in FIG. 12, the orthotic device 1200 incorporates a concave anterior maxillary abutment surface 1215 mounted via an arm 1220 to the extraoral member 1205. The length of the arm 1220 is adjustable via the action of knob 1260. As illustrated, the length of the extraoral member 1205 can be adjusted by the extraoral adjustment means 1255.

The extraoral member 1205 is connected to the intraoral body portion 1265 of the orthotic device by member 1210. The convex band shaped anterior mandibular abutment surface 1225 is connected to arm 1235 by a single member 1230. The length of member 1230 may be adjusted by the action of means 1275 to suit the patient's requirement.

The intraoral posterior maxillary abutment surfaces 1240 and 1240' are connected to intraoral body portion 1265 by single arm 1235 and by connecting arm 1270. The length of arm 1235 may be adjusted to suit the patient's requirements by the action of means 1280. Abutment surfaces 1240 and 1240' are flat projections which make contact with at least a portion of the maxillary surface and are attached to arm 1235 by posterior arm 1270. Abutment surfaces 1240 and 1240' have guide surfaces 1250 and 1250' respectively, which are positioned to make contact with the maxillary surfaces and help position the orthotic in the patient's mouth. The distance between surfaces 1240 and 1240' is variable via the action of means 1290.

Figure 13:
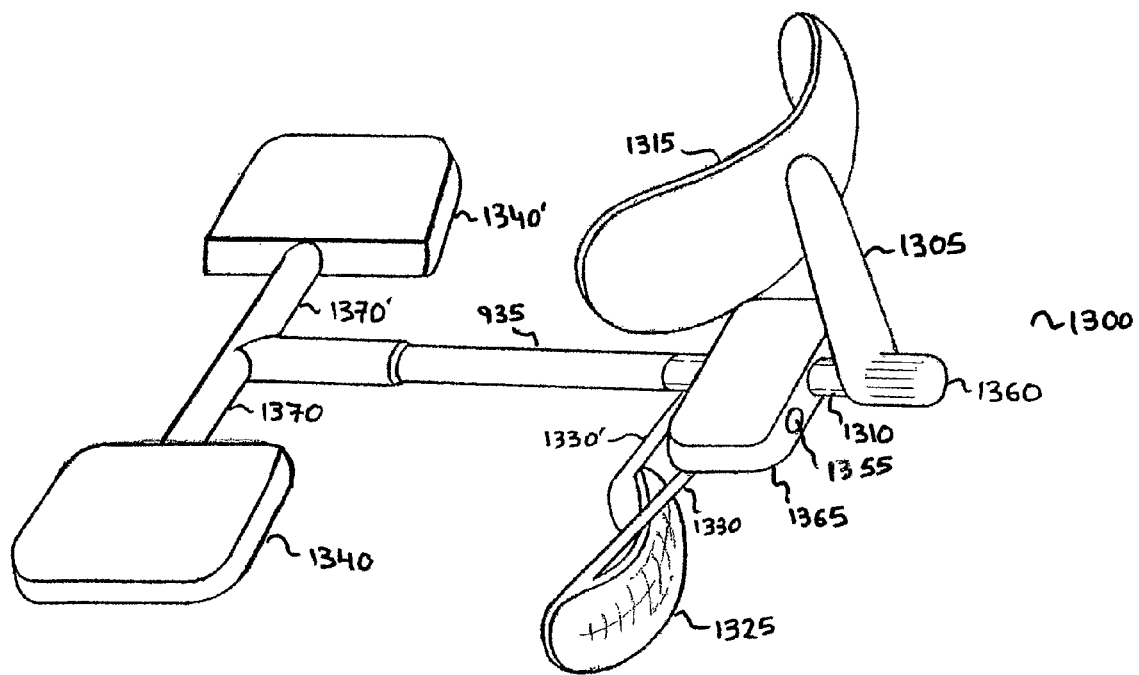
FIG. 13 is a perspective view of an orthotic device according to a thirteenth embodiment of the invention.

Referring to the thirteenth embodiment of the invention illustrated in FIG. 13, the orthotic device 1300 incorporates an intraoral concave anterior maxillary abutment surface 1315 mounted on intraoral member 1305. As illustrated, the position of the intraoral member 1305 can be adjusted by the adjustment means 1360.

The intraoral member 1305 is connected to the intraoral body portion 1365 of the orthotic device by member 1310. The convex band shaped anterior mandibular abutment surface 1325 is connected to body portion 1365 by members 1330 and 1330'. The position of the convex band shaped anterior mandibular abutment surface 1325 can be adjusted by movement of body portion 1365 along member 910. The angle and/or length of members 1330 and 1330' can also be adjusted to suit the user's requirements. As illustrated, an air hole 1355 is shown passing through intraoral body portion 1365 and is positioned to improve flow of air through and around the orthotic device.

The intraoral posterior maxillary abutment surfaces 1340 and 1340' are connected to intraoral body portion 1365 by single arm 1335 and by connecting arms 1370 and 1370'. The length of arm 1335 and connecting arms 1370 and 1370' can be adjusted to suit the patient's requirements.

The abutment surfaces 1340 and 1340' are flat projections which make contact with at least a portion of the maxillary surface. This contact resists rotation of the orthotic device 1300 produced by the interaction of the mandibular abutment surface 1325 and the anterior maxillary abutment surface 1315.

Figure 14:
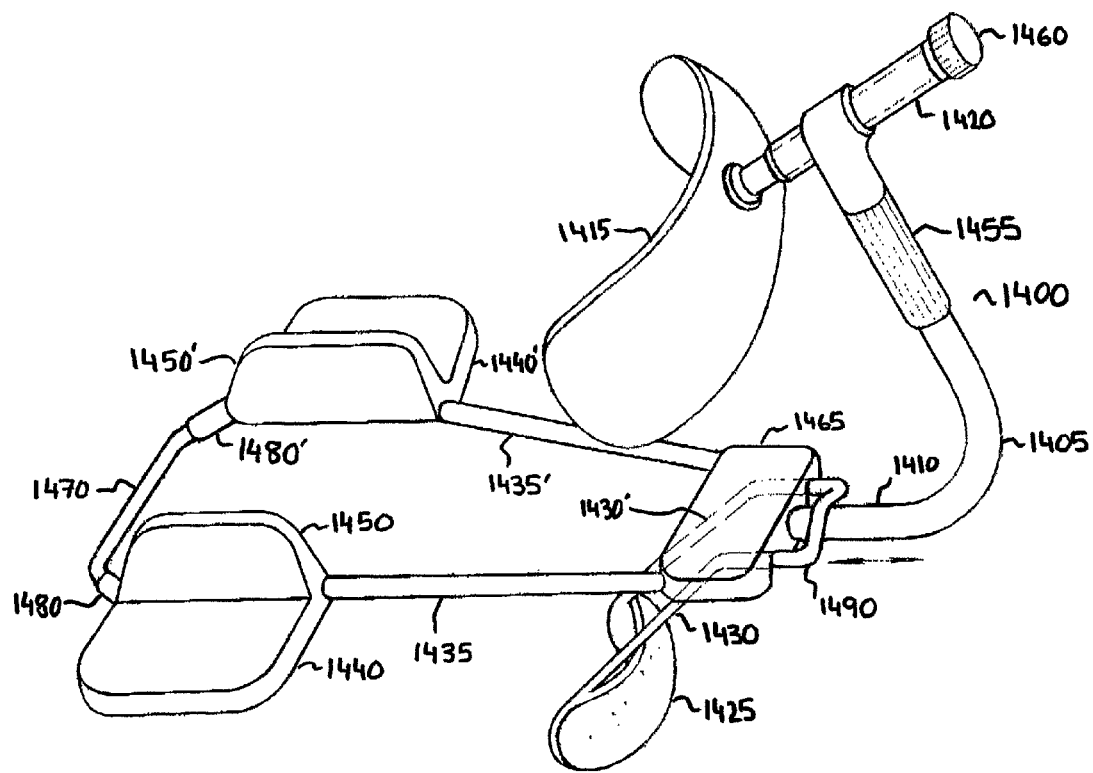
FIG. 14 is a perspective view of an orthotic device according to a fourteenth embodiment of the invention.

Referring to the fourteenth embodiment of the invention illustrated in FIG. 14, the orthotic device 1400 incorporates a concave anterior maxillary abutment surface 1415 mounted via a sliding arm 1420 to the extraoral member 1405. In this embodiment, the length of the arm is adjustable via the action of adjustment means 1460. As illustrated, the length of the extraoral member 1405 can be adjusted by the extraoral adjustment means 1455.

The extraoral member 1405 is connected to the intraoral body portion 1465 of the orthotic device by member 1410. The convex band shaped anterior mandibular abutment surface 1425 is connected to body portion 1465 by members 1430 and 1430'. The position of the convex band shaped anterior mandibular abutment surface 1425 can be varied according to the user's requirements by movement of connecting web portion 1490.

The intraoral posterior maxillary abutment surfaces 1440 and 1440' are connected to intraoral body portion 1465 by arms 1435 and 1435'. The abutment surfaces 1440 and 1440' make contact with at least a portion of the maxillary surface. This contact resists rotation of the orthotic device 1400 produced by the interaction of the mandibular abutment surface 1425 and the anterior maxillary abutment surface 1415.

Abutment surfaces 1440 and 1440' have guide surfaces 1450 and 1450' respectively, which are positioned to make contact with the maxillary surfaces and help position the orthotic in the patient's mouth.

With this embodiment, there is a connecting member 1470 linking the abutment surfaces 1440 and 1440'. This connecting member is adapted to contact and depress the user's tongue and has the advantage of improving the performance of the orthotic device for treating sleep apnoea in some patients. The position of connecting member 1470 can be adjusted by the action of adjustment means 1480 and/or 1480'.

The orthotic device for retaining a patient's mandible in a protrusive position embodying the invention can have a number of beneficial uses, including as an early interceptive device to encourage mandibular growth, in the treatment of certain orthodontic problems, in the treatment of certain temporomandibular joint problems, in the management of bruxism, and/or in the treatment of snoring and obstructive sleep apnoea.

The orthotic device can be formed from orthodontic materials such as acrylic, cobalt chromium, gold, silver, platinum or other acceptable materials.

In some circumstances, it may be desirable to add a simple tooth-stabilising plate, such as a retainer fitted to the orthotic device. This may serve to resist movement of the teeth due to engagement of the respective abutment surfaces, and also may avoid a degree of discomfort. The inclusion of such a plate may help to stabilize the upper and/or lower dentition.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. A dental orthotic device for retaining a patient's mandible in a protrusive position, the dental orthotic device comprising:
    a convex band-shaped intraoral anterior mandibular abutment surface for resisting mandibular retraction by abutting the patient's gingiva covering the mandible, wherein the intraoral anterior mandibular abutment surface does not encompass the teeth;
    an extramaxillary anterior maxillary abutment surface against which the intraoral anterior mandibular abutment surface is braced by means of the extramaxillary anterior maxillary abutment surface abutting the patient's tissue covering the subnasal maxillary bone;
    an intraoral posterior maxillary abutment surface to resist rotation of the dental orthotic produced by interaction on the patient of the intraoral anterior mandibular abutment surface and the extramaxillary anterior maxillary abutment surface.

2. The device of claim 1 wherein the anterior maxillary abutment surface is concave.

3. The device of claim 1 wherein the anterior maxillary abutment surface is of a shape to comfortably fit upon and conform to the shape of the tissue covering the maxillary bone.

4. The device of claim 1 wherein the anterior maxillary abutment surface is extraoral.

5. The device of claim 1 wherein the position of the anterior maxillary abutment surface is adjustable to give a variable extent of protrusion of the mandible.

6. The device of claim 5 wherein the positional adjustment is achieved by a screw extension device.

7. The device of claim 1 wherein the device further comprises a posterior tongue abutment surface which depresses at least a portion of the patient's tongue to avoid or at least minimize occlusion of the patient's airway.

8. The device of claim 7 wherein a position of the posterior tongue abutment surface is adjustable to give a variable extent of depression of at least a portion of the patient's tongue.

9. The device of claim 1 wherein the device has a cavity for accommodating at least a portion of the anterior section of the tongue.

10. The device of claim 9 wherein the cavity is adapted to hold the tongue in a protrusive position.

11. The device of claim 10 wherein the cavity comprises an upper tongue holding surface and a lower tongue holding surface.

12. The device of claim 11 wherein a combined biting force from the anterior maxillary and mandibular surfaces causes the tongue holding surfaces to securely hold the tongue in a protrusive position.

13. The device of claim 1 wherein the intraoral anterior mandibular abutment surface is of a shape to fit comfortably upon the gingiva covering the mandible.

14. The device of claim 13 wherein the intraoral anterior mandibular abutment surface is formed of an elastomeric material.

15. The device of claim 14 wherein the intraoral anterior mandibular abutment surface is formed of an elastomeric thermoplastic material.

16. The device of claim 15 wherein the elastomeric material is a silicone rubber.

17. The device of claim 1 wherein the device comprises at least one guide surface adapted to resist lateral movement of the orthotic device in the patient's mouth.

18. The device of claim 1 wherein the orthotic device comprises a soft palate abutment surface adapted to support the patient's soft palate.

19. The device of claim 18 wherein the soft palate abutment surface is of a shape to conform to the surface of the soft palate.

20. The device of claim 1 wherein air holes are provided in the device to facilitate airflow through the patient's airway.

21. The device of claim 1 further comprising a tooth stabilizing plate adapted to be fitted to the lower dentition and/or upper dentition.

22. A method of treating obstructive sleep apnoea, comprising:
    releasably fitting a dental orthotic device of claim 1 and
    maintaining protrusion of the mandible to at least minimize occlusion of the patient's airway.

23. A method for the treatment of one or more orthodontic conditions, snoring, obstructive sleep apnoea and temporomandibular joint disorders, the method comprising:
    releasably fitting a dental orthotic device of claim 1 and
    causing protrusion of the mandible.

24. A method of retaining a patient's mandible in a protrusive position, the method comprising:
    resisting retraction of the mandible by abutting on the patient's gingiva covering the mandible a convex band-shaped intraoral anterior mandibular abutment surface, which does not encompass the teeth;
    bracing the intraoral anterior mandibular abutment surface against an extramaxillary anterior maxillary abutment surface; and
    bracing against rotation produced by the interaction of the intraoral anterior mandibular abutment surface and the extramaxillary anterior maxillary abutment surface, with an intraoral posterior maxillary abutment surface.

25. The method of claim 24, further comprising depressing at least a portion of the patient's tongue to avoid or at least minimize occlusion of the patient's airway.

26. The method of claim 25 further comprising holding the tongue a protrusive position.

27. The method of claim 25 further comprising supporting the patient's soft palate.

28. The method of claim 24 further comprising holding the tongue a protrusive position.

29. The method of claim 24 further comprising supporting the patient's soft palate.

* * * * *